United States Patent [19]

Mori et al.

[11] Patent Number: 5,709,837
[45] Date of Patent: Jan. 20, 1998

[54] DRY ANALYTICAL ELEMENT CONTAINING AMPHOLYTE

[75] Inventors: Toshihiro Mori, Saitama; Masashi Ogawa, Kanagawa; Yoshikazu Amano, Saitama, all of Japan

[73] Assignee: Fuji Photo Film Co., Ltd., Kanagawa, Japan

[21] Appl. No.: 545,233

[22] Filed: Oct. 19, 1995

[30] Foreign Application Priority Data

Oct. 19, 1994 [JP] Japan .................. 6-253546

[51] Int. Cl.⁶ .................................... G01N 21/17
[52] U.S. Cl. ................... 422/56; 436/98; 436/108
[58] Field of Search ................... 422/56–58, 61; 436/98, 108

[56] References Cited

U.S. PATENT DOCUMENTS

| | | | |
|---|---|---|---|
| 4,066,403 | 1/1978 | Bruschi | 422/57 |
| 4,274,832 | 6/1981 | Wu et al. | 436/71 |
| 4,732,849 | 3/1988 | Seshimoto et al. | 422/56 |
| 5,008,078 | 4/1991 | Yaginuma et al. | 422/56 |
| 5,286,624 | 2/1994 | Terashima et al. | 422/56 |

FOREIGN PATENT DOCUMENTS

| | | |
|---|---|---|
| 0176357 | 4/1986 | European Pat. Off. . |
| 0444240 | 9/1991 | European Pat. Off. . |
| 0481436 | 4/1992 | European Pat. Off. . |

OTHER PUBLICATIONS

Derwent Publications Ltd., London, GB, AN 86–017024, XP002006272, & JP A-60 239,448 (Fuji Photo Film KK), Nov. 28, 1985.

Derwent Publication, AN 74-61025V XP002006273 & SU A 401 676 of Feb. 26, 1974.

Derwent Publications Ltd., AN 75-73253W, XP002006274 & JP A 50-072,691, Fujisawa Pharm. Ind. KK).

Database WPI—Section Ch, Week 8603—Derwent Publication Ltd., London, GB; AN 86-017024 & JP-A-60 239 448 (Fuji Photo Film KK), Nov. 28, 1985 (Abstract).

Database WPI—Section Ch, Week 7434—Derwent Publication Ltd., London, GB; AN 74-61025V & SU-A-401 676 (Gen Inorg Chem as Belrus) Feb. 26, 1974 (Abstract).

*Primary Examiner*—Lyle A. Alexander
*Attorney, Agent, or Firm*—McAulay Fisher Nissen Goldberg & Kiel, LLP

[57] ABSTRACT

A dry analytical element comprising at least one water-permeable reagent layer and a porous spreading layer laminated in this order on a support, wherein at least one layer which is the water-permeable reagent layer, the porous spreading layer or an optional water-permeable layer contains a water-soluble polybasic amino carboxylic acid which is an ampholyte. By applying an analytical element of the invention, an analyte can be measured at a high sensitivity using a small amount of an enzyme, etc., and shelf file can be extended.

20 Claims, 3 Drawing Sheets

F I G. 1

F I G. 2

F I G. 3

F I G. 4

F I G. 5

DRY ANALYTICAL ELEMENT CONTAINING AMPHOLYTE

BACKGROUND OF THE INVENTION

This invention relates to a dry analytical element suitable for the analysis of an aqueous liquid sample, particularly a biological body fluid, such as blood, cerebrospinal fluid, lymph, saliva or urine.

Dry analytical elements contain all reagents necessary for an analysis in a laminated sheet, and an analyte can be analyzed only by spotting a sample followed by incubating. Accordingly, the dry analytical element is an analytical means which has been widely spread rapidly.

The fundamental structure of the dry analytical element is, in general, composed of three layers, i.e. a porous spreading layer, a reagent layer and a transparent support, and accroding to the kind of analyte, etc., a light-blocking layer, a registration layer, a water-absorption layer or the like is further added.

Reagent compositions incorporated in dry analytical elements sometimes contain components having a different optimal reaction pH. For example, creatinine deiminase and glutamine dehydrogenase are incorporated into an analytical element for the analysis of creatinine disclosed in U.S. Pat. No. 5,286,624, and the optimal pH of both enzymes is different from each other.

In the above case, it is preferable to incorporate both enzymes into separate layers and the adjust the pH of each layer to the most preferred in view of stability and reactivity of each enzyme. However, it is difficult to arrange layers having a different pH in a thin analytical element having a total thickness thinner than 1 mm, particularly in the case of analytical elements wherein each layer is formed by coating an aqueous solution or suspension. Thereupon, in the case of preparing a dry analytical element containing two layer having a predetermined different pH, a device was made, e.g. one layer is provided by coating an aqueous solution, and then the other layer is provided by coating an organic solvent solution. Another means is to provide layers having a predetermined different pH by using a polymer acid difficult to diffuse and a polymer base difficult to diffuse, as disclosed in U.S. Pat. No. 4,604,347.

In the above dry analytical elements, the quantity of enzymes which are expensive must be increased, and moreover, inactivation of the enzymes during stock must been noted.

SUMMARY OF THE INVENTION

An object of the invention is to provide a dry analytical element, having a plurality of water-permeable layers, capable of arranging respective layers so as to have a different pH, and thereby capable of adjusting the pH of the layers to an optimum pH for each reagent component.

Another object of the ivnention is to provide a dry analytical element, containing a plurality of enzymes, capable of decreasing the quantity of the enzymes and of extending its shelf life.

The present invention provides a dry analytical element which has achieved the above objects, which comprises a dry analytical element comprising a porous spreading layer, a water-permeable reagent layer and a support laminated in this order, wherein at least one layer which is the water-permeable reagent layer, the porous spreading layer or an optional water-permeable layer contains a water-soluble polybasic amino carboxylic acid which is an ampholyte.

DETAILED DESCRIPTION OF THE INVENTION

The support can be a water-impermeable light-transmissive support used for a conventional known dry analytical element, and includes a transparent film or sheet made of polyethylene terephthalate, polycarbonate of bisphenol A, polystyrene, cellulose ester, such as cellulose diacetate, cellulose triacetate and cellulose acetate propionate, or the like. The thickness of the support is usually in the range of about 50 µm to about 1 mm, preferably from about 80 µm to about 300 µm. The support may be provided with an undercoating layer on its surface in order to strengthen the adhesion of the reagent layer laminated thereon. Instead of the undercoating layer, the surface of the support may be treated by a physical activation, such as, glow discharge or corona discharge or by a chemical activation.

On the support, the reagent layer is provided directly or through other layer(s) such as the undercoating layer. The reagent layer is a water-absorptive water-permeable layer wherein at least a part the reagent composition which reacts with an analyte in an aqueous sample to produce an optically detectable change described later is dispersed substantially uniformly in a hydrophilic polymer binder. The reagent layer includes indicator layer and dye-forming layer.

The hydrophilic polymer usable as the binder in the reagent layer is a natural or synthetic hydrophilic polymer having a swelling ratio in the range of about 1.5 to about 20 preferably from about 2.5 to about 15 at a water absorption at 30° C. Illustrative of the hydrophilic polymer are gelatins, such as acid-treated gelatin and deionized gelatin, gelatin derivatives, such as phthalated gelatin and hydroxyacrylate-graft gelatin, agarose, pullulan, pullulan derivatives, polyacrylamide, polyvinyl alcohol and polyvinylpyrrolidone.

The reagent layer may be a crosslinked (cured) layer to a certain degree by adding a crosslinking agent. Illustrative of the crosslinking agents are known vinyl sulfonyl crosslinking agents, such as 1,2-bis(vinylsulfonyl acetamide)ethane and bis(vinylsulfonylmethyl)ether, aldehydes and the like for gelatin, aldehydes, epoxy compounds having 2 glycidyl groups, and the like for methallyl alcohol copolymers.

A suitable dry thickness of the reagent layer is about 1 μm to about 100 μm, preferably about 3 μm to about 30 μm. The reagent layer is preferably transparent.

A light-blocking layer can optionally be provided on the reagent layer. The light-blocking layer is a water-permeable layer wherein light-absorptive or light-reflecting (called "light-blocking" collectively) particles are dispersed in a small amount of hydrophilic polymer having a film-forming ability as a binder. The light-blocking particles block the color of the sample spotted on the spreading layer described later, particularly the red color of hemoglobin in the case of whole blood samples, when a detectable change, such as color change or coloration, produced in the reagent layer is measured from the side of the light-transmissive support by reflection photometry. This layer also functions as a light-reflecting layer or a background layer. Illustrative of light-reflecting particles are titanium dioxide particles which are microcrystalline particles in rutile type, anatase type or brookite type having a particle size of about 0.1 μm to about 1.2 μm, barium sulfate particles and aluminum particles or microflakes, and illustrative of light-absorptive particles are carbon black, gas black and carbon microbeads. Preferred particles are titanium dioxide particles and barium sulfate particles, and anatase type titanium dioxide particles are particularly preferred. The hydrophilic polymer binder having a film-forming ability includes the foregoing hydrophilic polymers usable for the reagent layer, weakly hydrophilic regenerated cellulose and cellulose acetate. Preferable hydrophilic polymers are gelatins, gelatin derivatives and polyacrylamide. A known curing agent (crosslinking agent) may be added to the geglatin or a gelatin derivative. The light-blocking layer may be formed by applying an aqueous solution of a hydrophilic polymer wherein light-blocking particles are suspended followed by drying. Instead of providing the light-blocking layer, the light-blocking particles may be incorporated in the spreading layer described layer.

An adhesive layer may be provided on the reagent layer or an optional layer, such as the light-blocking layer, in order to join the spreading layer. The adhesive layer is preferably composed of a hydrophilic polymer which can join the spreading layer thereby to integrate respective layers upon moistened or absorbing water to swell. Illustrative of the hydrophilic polymers usable for the production of the adhesive layer are the aforementioned hydrophilic polymers usable for the production of the reagent layer. Preferable ones are gelatin, gelatin derivatives and polyacrylamide. A suitable dry thickness of the adhesive layer is, in general, about 0.5 μm to about 20 μm, preferably about 1 μm to about 10 μm. The adhesive layer may also be provided on other layer(s) in order to improve adhesive force between other layers, in addition to the reagent layer. The adhesive layer can be formed by applying an aqueous hydrophilic polymer solution, to which a surfactant or the like is optionally added, onto the support, the reagent layer or the like by a known method.

The porous spreading layer may be a woven fabric spreading layer disclosed in U.S. Pat. No. 4,292,272, U.S. Pat. No. 4,783,315, etc., such as, plain weaves including broad cloth and poplin, a knitted fabric spreading layer disclosed in EP 0 162 302 A, etc., such as tricot, double tricot or milanese, a spreading layer made of a woven fabric or knitted fabric etched by an alkaline etching solution disclosed in Japanese Patent KOKAI 1-172753, a spreading layer made of organic polymer fiber pulp-containing paper disclosed in U.S. Pat. No. 5,215,716, a nonfibrous isotropic porous spreading layer, such as a membrane filter (blushed polymer layer) disclosed in U.S. Pat. No. 3,992,158, a continuous microspaces-containing porous layers where polymer particulates, glass particulates or diatomaceous earth are dispersed in a hydrophilic polymer binder, or a continuous microspaces-containig porous layer where polymer particulates are joined so as to contact with each other at a point by using a polymer adhesive which does not swell in water (three-dimensional lattice structure layer), or the like.

Two or more spreading layers may be incorporated. For example, two or more porous layers which are joined by an adhesive disposed in spots, such as disclosed in Japanese Patent KOKAI 61-4959, 62-138756, 62-135757 or 62-138758.

A spreading controller, such as a hydrophilic polymer may be incorporated into the spreading layer in order to control spreading ability. Various reagents or a part of reagent(s) may also be incorporated for the purpose of accelerating object detecting reaction or reducing or inhibiting interfering reaction(s).

A suitable thickness of the spreading layer is 20 to 200 μm, preferably 50 to 170 μm, more preferably 80 to 150 μm.

Physical activation treatment represented by glow discharge or corona discharge disclosed in U.S. Pat. No. 4,783,315 may be provided at least one side of the woven fabric, knitted fabric or paper used as the porous spreading layer. The woven fabric, knitted fabric or paper may be treated with degreasing by washing with water, or impregnating with a surfactant or a hydrophilic polymer. By providing the fabric or paper with one or more of the above treatment, the fabric or paper is rendered hydrophilic, and the adhesive force to the layer located on the underside, i.e. near the support, can be increased.

A water absorption layer may be provided between the support and the reagent layer. The water absorption layer is mainly composed of a hydrophilic polymer which absorbs water to swell, and it absorbs the water of aqueous liquid sample which reaches the surface of this layer. In the case of whole blood sample, it accelerates permeation of blood plasma component into the reagent layer. The hydrophilic polymer usable for the water absorption layer can be selected from the aforementioned ones usable for the reagent layer. Preferred hydrophilic polymers for the water absorption layer are, in general, gelatin, a gelatin derivative, polyacrylamide and polyvinyl alcohol, particularly the aforementioned gelatins and deionized gelatin, and the aforementioned same gelatins as the reagent layer are the most preferable. The dry thickness of the water-absorption layer is about 3 μm to about 100 μm, preferably about 5 μm to about 30 μm. The coating weight of the water-absorption layer itself is about 3 $g/m^2$ to about 100 $g/m^2$, preferably about 5 $g/m^2$ to about 30$g/m^2$. By incorporating a pH buffer, basic polymer or the like described later into the water absorption layer, pH upon use (conducting analytical operations) can be adjusted. Moreover, a known mordant, polymer mordant, etc. may be incorporated into the water absorption layer.

In the case of analyzing ammonia, a liquid barrier layer is provided on a first reagent layer (indicator layer). The liquid barrier layer is composed of a microporous material having penetrated pores which substantially do not pass liquid components and interfering substances dissolved in the liquid components, such as alkaline components, of a coating solution and a sample liquid but passes gaseous ammonia through manufacturing the dry analytical element and/or through analytical operations. It is preferable that the microporous material is made of a hydrophobic material where cupillary phenomenon by liquid, particularly water, substantially does not occur or made of a material rendered hydrophobic or water-repellent to the degree not to generate capillary phenomenon.

The water-repellent treatment the microporous material can be conducted by using a common agent used for hydrophobic treatment or a common water repellent, represented by silicone resin, silicone oil, fluorine contained resin and fluorine contained oil as it is or optionally diluted with a solvent, such as, hexane, cyclohexane or petroleum ether in a solid content of about 0.1 to 5 wt. %, and applying it onto at least one surface and the neighborhood of the micro porous material having continuous pores by immersing, coating or spraying.

Illustrative of the micro porous materials are a membrane filter, a microporous material formed by a fibrous material entangled with, adhered to or bonded to each other, such as paper, filter paper, felt or nonwoven fabric, a micro porous material composed of a woven fabric, a knitted fabric or a fine net material.

The membrane filters usable as the liquid barrier layer are those produced by using a cellulose acetate, cellulose nitrate, regenerated cellulose, polyamide, polycarbonate of bisphenol A, polyethylene, polypropylene, fluorine-containing polymer, such as polytetrafluoroethylene, or the like or optionally provided with water-repellent treatment.

In the case of using the membrane filter for the dry analytical element of the invention, a suitable thickness is in the range of usually about 30 to 300 μm, preferably 70 to 200 μm. The porosity (void content) of the membrane filter is usually about 25 to 90%, preferably about 60 to 90%. The mean pore size of the membrane filter is in the range of usually about 0.01 to 20 μm, preferably about 0.1 to 10 μm. Various membrane filters are supplied by many manufactures, and the membrane filter can be selected therefrom.

The microporous material is adhered to the aforementioned indicator layer with a practical strength. The above adhesion can be conducted by adhering the micro porous material to the indicator layer in a wet state, and then drying. The indicator layer in a wet state means that the binder is in a swelled state, dispersed state or solution state by the solvent used for dissolving the binder polymer which still remains or wetting the dried membrane with a soluble solvent.

On the liquid barrier layer, a second reagent layer (ammonia-producing reagent layer) containing a reagent reacting with an ammonia-producing substrate to produce ammonia is provided.

On the second reagent layer, it is preferable to provide an ammonia diffusion-preventing layer which has an ability substantially to prevent (or hinder) the ammonia produced in the second reagent layer from diffusing into the endogeneous ammonia-trapping layer described layer and which substantially does not conduct trapping of ammonia and ammonia-producing reaction. The ammonia diffusion-preventing layer may be replaced by another layer having a different function which substantially does not conduct trapping of ammonia and ammonia-producing reaction. The layer having a different function includes a hardened (or cross-linked) hydrophilic polymer layer, a light-blocking layer and an adhesive layer.

In the case of the analytical element for the determination of an ammonia-producing substance, such as creatinine, it is preferable to provide an endogeneous ammonia-trapping layer containing reagent acting on the ammonia already present in an aqueous liquid sample (endogeneous ammonia) to convert to the state substantially impossible to reach the aforementioned reagent layer, on the ammonia diffusion-preventing layer directly or through the aforementioned light-blocking layer or another intermediate layer. The endogeneous ammonia-trapping layer has a function of trapping the coexisting endogeneous ammonia, prior to the occurrence of the reaction producing ammonia by reaching of the analyte of an ammonia-producing substance, such as, creatinine or urea nitrogen, to the reagent layer.

An the endogeneous ammonia-trapping reagent, the reagent compositions containing an enzyme having a catalystyc ability acting on ammonia as a substrate to convert it to another substance are preferred. Examples of the endogeneous ammonia-trapping reagent are reagent compositions containing NADH (nicotinamide adenine dinucleotide in reduced form) and/or NADPH (nicotinamide adenine dinucleotide phosphate in reduced form), glutamate dehydrogenase (EC 1.4.1.3; GLDH) and α-ketoglutaric acid or its sodium salt (α-KG). Reagent compositions containing aspartase (EC 4.3.1.1) and fumaric acid or a fumarate salt may also be usable. In the integral multilayer analytical element of the invention, it is preferable to use a reagent composition contaning NADH, GLDH and α-KG as the endogeneous ammonia-trapping reagent. In the case of using a reagent composition containing GLDM or a reagent composition containing aspartase, it is preferable to use a suitable buffer so as to maintain the pH value of the endogeneous ammonia-trapping layer to usually not higher than 10.0, preferably in the range of 7.0 to 9.5.

It is a matter of course that, when the analytical element is for the determination of ammonia, the endogeneous ammonia-trapping layer is not provided.

The dry analytical element of the invention is characterized in that a particular ampholyte is incorporated into at least one of water-permeable layer in a dry analytical element mention heretofore. Ampholytes suitable for the invention are disclosed in Acta Chemica Scandinabvica, vol. 20, p 820, 1966, : bid., vol. 23, p 2653, 1969, Denkieido Gakkai (Society of Electrophoresis). "Denkieido Jikken-Ho (Experimental Method of Electrophoresis), Revised 5th Edition", pp 249–252, Bunko-Do, Tokyo, 1976, Japanese Patent KOKAI 60-239448, etc. Preferable ampholytes includes those disclosed in Japanese Patent KOKAI 60-239448, "Ampholine Carrier Ampholytes" (LKB Produkter), etc. The ampholytes disclosed in Japanese Patent KOKAI 60-239448 (Chemical Abstracts, Vol. 105 (1986): 21319n) are water-soluble polybasic amino carboxylic acid synthesised by allowing an organic compound having at least two amino or imino groups reacting with a carboxylic acid ester having a carbon-carbon double bond in a nonaqueous solvent, and then hydrolyzing the ester portion.

The organic compound having at least two amino or imino groups is represented by the following general formula [I]:

In the formura, R represents a divalent group which may contain a monovalent or polyvalent group represented by the formula >N—R⁵, and R¹, R², R³, R⁴ and R⁵ represent hydrogen atom, alkyl group or substituted alkyl group, independently, provided that at least one of R¹, R², R³, R⁴ and R⁵ is hydrogen atom. Each of R¹, R², R³, R⁴ and R⁵ is preferably selected from hydrogen atom, methyl group, ethyl group, n-propyl group, isopropyl group, n-butyl group, i-butyl group, t-butyl group, hydroxymethyl group and hydroxyethyl group. Preferable R groups are polymethylene groups having a number of carbon atoms 6 or less and polymethylene groups containing a monovalent or polyvalent group represented by >N—R⁵ in the chain, provided that one or more methylene groups may be substituted ones with the above R¹, R², R³, R⁴ and R⁵. Illustrative of the organic compounds represented by the general formula [I] are diethylenetriamine, triethylenetetramino, tetraethylenepentamine, pentaethylenehexamine, propylene amines corresponding to the above ethylene amines, etc. Particularly preferred one is pentaethylenehexamine.

The carboxylic acid ester having a carbon-carbon double bond is represented by the following general formula [II]:

In the formula, R⁶ and R⁷ represents hydrogen atom or lower alkyl group, independently. R⁸ represents hydrogen atom, cyano group or lower alkyl group. X represents single bond or divalent lower alkylene group.

R⁶, R⁷, R⁸, or X may contain monovalent —COOR¹⁰ group.

R⁹ and R¹⁰ represent lower alkyl group which may be substituted one, independently.

Preferable groups represented by R⁹ or R¹⁰ are methyl group, ethyl group, n-propyl group, isopropyl group, hydroxyethyl group and methoxyethyl group. Preferable compounds represented by the general formula [II] are α,β-unsaturated carboxylic acid esters, and illustrative thereof are methyl acrylate, ethylacrylate, n-propyl acrylate, methoxyethyl acrylate, and methacrylate esters, maleate esters and itaconate esters corresponding thereto. etc. Particularly preferred one is methyl acrylate.

The polybasic amino carboxylic acid used in the invention is synthesized by allowing the compounds represented by the general formula [I] or [II] to react in a nonaqueous solvent, and then hydrolyzing the ester portion.

As the nonaqueous solvent, alcohols, such as methanol and ethanol, ethers, such as diethyl ether, tetrahydrofuran and dioxane, nonprotonic polar solvents, such as acetonitrile and N,N-dimethylformamide, and halogenated hydrocarbons can be listed, and preferred ones are alcohols.

Reaction temperature and time may be set according to starting raw materials and reaction solvent, but less of them are better in view of less coloring of the object product. Catalyst (organic or inorganic acid or base) or polymerization inhibitor may optionally be added.

The type of the polyaminopolycarboxylic acid ester is determined according to the total number of the hydrogen atoms of non-substituted amino group in the compound of the formula [I] and the number of the compounds of the formula [II].

In the hydrolysis, in general, water is used as solvent, and optionally, inorganic or organic base or the like can be used as catalyst. In order to prevent products from coloring, it is preferable to conduct reaction in a inert gas (nitrogen gas, argon gas. etc.) under ordinary pressure or pressurized conditions, and it is also effective to conduct under reducing conditions, such as hydrogen gas and palladium-carbon.

Illustrative of the polybasic amino carboxylic acids are those represented by the general formula wherein R is H or —(CH₂)ₘCOOH,
provided that m is 1 or 2, preferably 2, and n is 3, 4 or 5, preferably 5.

The acidity or alkalinity of the polybasic amino carboxylic acid thus obtained can be adjusted by selecting charging molar ratio of the compounds represented by the general formula [I] or [II], or by controlling hydrolysis conditions to change hydrolysis rate. Thus, the acidity (or alkalinity) of the polybasic amino carboxylic acid is set so as to function as a buffer capable of adjusting to an optimum reaction pH desired by the layer into which the polybasic amino carboxylic acid is incorporated.

The acidity is adjusted by controlling the molar ratio of —COOH group to —NH₂ group. That is, upon the synthesis of the polybasic amino carboxylic acid, the molar ratio of —COOH group to —NH₂ group is adjusted so as to become a desired pH value. The ratio —COOH/—NH₂ of 1/6 results in about pH 9.5, 2/6 results in about pH 8.0, 4/6 results in about pH 7.0, and 6/6 results in about pH 5.0.

A suitable content of the polybasic amino carboxylic acid is about 0.5 to 50%, preferably about 1 to 5%.

The polybasic amino carboxylic acid is incorporated into one or more layers containing a component of which the reaction pH is desired to be controlled to an optimum pH, which are, in general, reagent layers (indicator layer, dye-forming layer, etc.). It is a matter of course, when another layer is allowed to function also as a reagent layer, the layer is also an object layer.

In the dry analytical element of the invention, reagent(s) are incorporated according to the type of the analyte to be measured, etc. For example, in the case of analyzing calcium, a known chelate indicator is used as the indicator in a reagent composition incorporated into reagent layer(s). Illustrative of the chelate indicators for the analysis of calcium are those described in "Dotite Reagents General Catalog 12th Ed." (Dojindo Laboratories, Kumamoto, Japan. 1980), which are o-Cresolphthalein Complexone (3,3'-bis[[di(carboxymethyl)amino]methyl]-o-cresolphthalein [2411-89-4], Eriochrome Black T (monosodium salt of 1-(1-hydroxy-2-naphthylazo)-6-nitro-2-hydroxynaphthalene-4-sulfonic acid [1787-61-7]), Methylthymol Blue Complexone (tetrasodium salt of 3,3'-bis[[di(carboxymethyl)amino]methyl]thymolphthalein [1945-77-3]), Thymolphthalein Complexone(3,3'-bis[[di-(carboxymethyl)amino]methyl]thymolphthalein [1913-93-5]), chlorophosphonazo-III(2,7-bis[(4-chloro-2-phosphonophenyl)azo]-1,8-dihydroxynaphthalene-3,6-disulfonic acid [1914-99-4]), chlorophosphonazo-I (disodium salt of 3-[4-chloro-2-phosphonophenyl)azo]-4,5-dihydroxy-2,7-naphthalenedisulfonate [1938-82-5],etc. Figures in the above angular brackets represent Chemical Abstracts Registry Number. Among these, o-Cresolphthalein Complexone and Chlorophosphonazo-III are preferable due to the most accurate determination of both total calcium and calcium ion. Optionally, the reagent composition may be divided and incorporated into two or more separate layers (e.g. reagent layer and water absorption layer).

In the dry analytical element for anlysis of calcium, a masking agent for masking magnesium ion is preferably incorporated. Such a masking agent includes 8-hydroxyquinoline, 8-hydroxyquinoline -5-sulfonic acid, 8-hydroxyquinoline-4-sulfonic acid, 8-hydroxyquinoline sulfate and the like. Suitable layers for incorporating the masking agent are reagent layer and/or its upper (far from the support) intermediate layer, adhesive layer or the spreading layer. The content of the masking agent is about 1.5 to about 10 times, preferably, about 2 to about 5 times, the content of the indicator.

In the case of analyzing calcium, a suitable buffer, capable of buffering an environmental pH to a desired value in the range of about 3.0 to 12.0, preferably 4.0 to 11.5, upon conducting analytical operations by spotting an aqueous liquid sample, is selected. The pH buffer is incorporated into at least one layer of reagent layer, water absorption layer, intermediate layer or adhesive layer located on the underside of the spreading layer (near the support). Preferable layers are reagent layer(s) and/or water absorption layer.

The pH buffers suitable for dry analytical elements are described in "Kagaku Benran Kiso-Hen" pp 1312–1320, Maruzen, Tokyo, 1966, R. M. C. Dawson et al, "Data for Biochemical Research", 2nd Ed., pp 476–508, Oxford at the Clarendon Press, 1969, "Biochemistry", Vol. 5, from pp 467–477, 1966 and "Analytical Biochemistry", Vol. 104, pp 300–310, 1980. Illustrative of the pH buffers in the range of pH 3.0 to 12.0 are 2-(N-morpholino)ethanesulfonic acid (MES); 3,3-dimethylglutaric acid, imidazole; buffers containng tris(hydroxymethyl)aminomethane, buffers containing a phosphate, buffers containing a borate, buffers containing a carbonate; buffers containing glycine; N,N-bis (2-hydroxyethyl)glycine (Bicine); N-(2-hydroxyethyl) piperazine-N'-2-hydroxypropane-3-sulfonic acid (HEPPS), soidum and pottasium salt thereof, N-2-hydroxyethylpiperizine-N'-2-ethanesulfonic acid (HEPES), sodium and potassium salt thereof, N-[tris(hydroxymethyl) methyl]-3-amino-propanesulfonic acid (TAPS), sodium and potassium salt thereof; β-hydroxy-4-(2-hydroxyethyl)-1-piperazinepropanesulfonic acid (HEPPSO), sodium and potassium salt thereof; 3-(cyclohexylamino)-1-propanesulfonic acid (CAPS), sodium and potassium salt thereof; and combinations of any of them and optional acid, alkali or salt. Preferable buffers include MES, 3,3-dimethylglutaric acid, imidazole, Tris-sodium borate, Bicine, HEPPS and sodium salt thereof, HEPPSO and sodium salt thereof, TAPS and sodium salt thereof, CAPS and sodium salt and potassium salt thereof, and the like.

In the case of analyzing ammonia, coloring ammonia indicators include leuco dyes, such as leuco cyanine dye, nitro-substituted leuco dye and leuco phthalein dye, disclosed in U.S. Re. Pat. No. 30 267 or Japanese Patent KOKOKU 58-19062, pH indicators, such as Bromophenol Blue, Bromocresol Green, Bromthymol Blue, Quinoline Blue and rosolic acid disclosed in "Kagaku Dai Jiten, (Encyclopaedia Chimica)", vol. 10, pp 63–65, Kyoritsu Shuppan, Tokyo, 1962, triarylmethane dye precursors, leuco benzylidene dyes disclosed in Japanese Patent KOKAI 55-379 or 56-145273, diazonium salts and azo couplers, and alkali-bleachable dyes. A preferable-blending amount of the coloring ammonia indicator is about 1 to 20 wt. % of the weight of the binder.

The reagent reacting with an ammonia-producing substance to produce ammonia is prefeably an enzyme or a reagent containing an enzyme, and the enzyme suitable for the analysis can be selected according to the type of the ammonia-producing substance which is the analyte. In the case of using an enzyme as the above reagent, the combination of ammonia-producing substance and reagent is decided by the specificity of the enzyme. Examples of ammonia-producing substance/reagent are urea/urease, creatinine/creatinine deiminase, amino acid/amino acid dehydrogenase, amino acid/amino acid oxidase, amino acid/ ammonia lyase, amine/amine oxidase, diamine/amine oxidase, glucose and phosphoamidate/phosphoamidate hexose phosphotransferase, ADP/carbamate kinase and carbamoylphosphate, acid amide/amide hydrolase, nucleobase/nucleobase deaminase, nucleoside/nucleoside deaminase, nucleotide/nucleotide deaminase, guanine/ guanase, etc. Alkaline buffers usable for the reagent layer are usually in the range of pH 7.0 to 12.0, preferably 7.5 to 11.5.

In the case of analyzing glucose, illustrative of the reagent compositions are modified Trinder reagent Compositions comprising glucose oxidase, peroxidase, 4-aminoantipyrine or a derivative thereof and 1,7-dihydroxynaphthalene, disclosed in U.S. Pat. No. 3,992,158, Japanese Patent KOKAI 54-26793, 59-20853, 59-46854, 59-54962, etc.

The reagent layer in the case of analyzing ammonia can contain optionally a wetting agent, a binder crosslinking agent (curing agent), a stabilizer, a heavy metal ion trapping agent (chelating agent), and the like, in addition to the reagent reacting with an ammonia-producing substance to produce ammonia, the alkaline buffer and the hydrophilic polymer binder having a film-forming ability. The heavy metal ion trapping agent is used for masking the heavy metal ion which inhibits enzyme activity. Examples of the heavy metal ion trapping agent are complexanes, such as, EDTA·2Na, EDTA·4Na, nitrilotriacetic acid (NTA) and diethylenetriaminepentacetic acid.

A surfactant may be incorporated in the reagent layer, the water absorption layer, the ammonia diffusion-hindering layer, the endogeneous ammonia-trapping layer, the light-reflecting layer, the adhesive layer, the intermediate layer, the spreading layer containing or not containing the ammonia-trapping reagent composition, etc. A suitable surfactant is a nonionic surfactant, such as, p-octylphenoxypolyethyoxyethanol, p-nonylphenoxypolyethoxyethanol, polyoxyethylene oleyl ether, polyoxyethylenesorbitanmonolaurate, p-nonylphenoxypolyglycidol, octylglucoside, etc. The spreading action (metering action) for spreading an aqueous liquid sample is improved by adding a nonionic surfactant to the spreading layer. The water in an aqueous liquid sample is easily substantially uniformly absorbed by the reagent layer or a water absorption layer by adding a nonionic surfactant to these layers during analytical operations, and the liquid contact with the spreading layer becomes rapid and substantially uniform.

A hemolytic reagent can be incorporated into the spreading layer. The hemolytic reagent hemolyzes whole blood, i.e. to destroy or dissolve cell membrane of components having cell membrane (also called solid components), such as erythrocytes and leukocytes, to effuse their contents into plasma. Representative hemolytic reagents are surfactants having hemolytic ability and combinations of hemolysin and complement which are immunological components, e.g. a combination of rabbit and sheep blood cell antibody and guinea pig complement. As the surfactants, there are nonionic surfactants, cationic surfactants and anionic surfactants, and nonionic surfactants are preferred. It is known to incorporate 5 to 11 g/m$^2$ of a nonionic surfactant into the spreading layer of a dry analytical element (Japanese Patent KOKAI 61-85200). However, the dry analytical element is made in order to remove effects of triglycerides in the analysis of total cholestrol using serum samples, and to hemolyze whole blood sample is not disclosed.

Preferable nonionic surfactants are alkylphenolpolyethyleneoxide condensates, such as p-(1,1,3,3-tetramethylbutyl) phenoxypolyethoxyethanol, Triton X-100 (containing 9–10 hydroxyethylene units on average), Triton X-165 (containing 16 hydroxyethylene, units on average), Triton X-405 (containing 40 hydroxyethylene units on average) (every number is chemical Abstract Registry No. 9002-93-1), alkylphenolpolyglycidol condensates, such as p-nonylphenoxypolyglycidol (containing 10 glycidol units on average), higher fatty alcohol polyethylene oxide condensates, such as lauryl alcohol polyethylene oxide condensates (Brij 35, Chemical Abstract Registry No. 9002-92-0), cetyl alcohol polyethylene oxide condensates (Brij 58, Chemical Abstract Registry No. 9004-95-9), polyethylene glycol higher fatty acid ester condensates, such as stearic acid ester polyethylene glycol condensates (e.g. Myrj 52, Myrj 59, both are Chemical Abstract Registry No. 9004-99-3), and higher fatty acid sorbitan ester polyethylene glycol condensates, such as sorbitan monolauric acid ester polyethylene glycol condensates (e.g. Tween 20, Chemical Abstract Registry No. 9005-64-5). In order to accelerate spreading of sample, an aforementioned nonionic, anionic, cationic or ampholyte surfactant may be incorporated into the spreading layer. A suitable hemolytic reagent content of the spreading layer is about 1 to 50 $g/m^2$, preferably about 2 to 20 $g/m^2$.

The hemolytic reagent can be incorporated into the spreading layer by dissolving or dispersing into a polymer solution for controlling spreading, and then, the polymer solution is applied onto the spreading layer. The solvent in the polymer solution may be water, organic solvent, water-organic solvent mixture, and the like, and the organic solvent may be methanol, ethanol, isopropanol, etc.

The dry analytical element of the invention can be prepared according to a known method. The polybasic amino carboxylic acid may be previously added to an aqueous reagent solution to be applied or impregnated. Another means is, in the case of being impregnated into the spreading layer, of impregnating an aqueous solution an organic solvent (ethanol, methanol, etc.) solution or a water-organic solvent mixture solution, contanining the polybasic amino carboxylic acid alone or further containing a surfactant, a hydrophilic polymer for controlling spreading area, etc. by applying from the upside of the spreading layer.

The analysis of an analyte can also be carried out according to a known method.

By applying an analytical element of the invention, an analyte can be measured at a high sensitivity using a small amount of an enzyme, etc., and shelf file can be extended.

EXAMPLES

The ampholyte used in the following examples was prepared according to the process of the example 1 of Japanese Patent KOKAI 60-239448. The isoelectric point of the ampholyte was 8.2.

Example 1

An indicator layer was provided by applying the following composition using ethanol as the solvent onto a colorless transparent smooth polyethylene terephthalate film (support) 180 μm in thickness so as to become the coating amount described in Table 1, followed by drying.

TABLE 1

| Indicator Layer Composition | |
| --- | --- |
| Polyvinyl methyl ether weight average molecular weight: about 40,000 | 2.2 $g/m^2$ |
| Bromophenol Blue | 0.14 $g/m^2$ |
| Sodium hydroxide | 8.4 $g/m^2$ |

A liquid barrier layer was provided thereon by pressing uniformly a membrane filter made of polyethylene having an average pore size of 0.2 mm, a void content of 75% and a thickness of 100 μm.

An ammonia-producing reagent layer was provided further thereon by applying the following composition using water as the solvent so as to become the coating amount described in Table 2, followed by drying.

TABLE 2

| Ammonia-Producing Reagent Layer Composition | |
| --- | --- |
| Hydroxyethyl cellulose average molecular weight: about 40,000 average substitution degree; 1.0–1.3 | 5 $g/m^2$ |
| Sodium tetraborate | 1 $g/m^2$ |
| Creatinine iminohyrolase (E.C. 3,5,4,21) Optimum pH: 9.0 | 1,800 $U/m^2$ |

(pH 9.0)

An ammonia diffusion-preventing layer was provided by applying the following composition using water as the solvent so as to become the following coating amount, followed by drying.

| Hydroxypropyl cellulose methoxyl group: 28–30% hydroxypropoxyl groupo: 7–12% viscosity of 2% aqueous solution: 50 cps at 20° C. | 20 $g/m^2$ |
| --- | --- |

An endogeneous ammonia-trapping layer was provided thereon by applying the following composition using water as the solvent so as to become the coating amount described in Table 3, followed by drying.

TABLE 3

| Endogeneous Ammonia - Trapping Layer Composition | |
| --- | --- |
| Hydroxyethyl cellulose | 4 $g/m^2$ |
| Ampholyte* | 1 $g/m^2$ |
| α-Ketoglutaric acid.2Na salt | 1 $g/m^2$ |
| NADPH | 0.6 $g/m^2$ |
| glutamate dehydrogenase (E.C. 1,4,1,4) optimum pH: 8.0 | 10,000 $U/m^2$ |

(pH 8.2)

*R—NH$(\text{CH}_2\text{CH}_2\text{N})_{\overline{5}}$H
         |
         R

R:H or —$CH_2CH_2COOH$
—COOH: —NH— and —$NH_2$ = 2:6

Subsequently, the endogeneous ammonia-trapping layer was damped by supplying 30 $g/m^2$ of water, and a tricot knitted fabric made of pure polyethylene terephthalate (knitted by spun yarn corresponding to 100 S) about 250 μm in thickness was laminated thereon by pressing lightly and almost uniformly. Polyvinylpyrrolidone (average molecular weight: 360,000) was impregrated into the knitted fabric by applying as an ethanol solution and then dried to provide a spreading layer.

Thus, a dry analytical element for the determination of creatinine was completed.

Comparative Example 1

A dry analytical element for the determination of creatinine was prepared similar to Example 1, except that the composition of Table 4 was used instead of the endogeneous ammonia-trapping layer composition.

TABLE 4

| | |
|---|---|
| Hydroxyethyl cellulose | 4 g/m² |
| Sodium tetraborate | 1 g/m² |
| α-Ketoglutaric acid.2Na salt | 1 g/m² |
| NADPH | 0.6 g/m² |
| Glutamate dehydrogenase | 10,000 U/m² |

Measurement 1

In order to examine endogeneous ammonia-trapping ability of the dry analytical element of Example 1 and Comparative Example 1, the following test was conducted.

10 μL of each control serum containing creatinine in a concentration shown in Table 5 was spotted onto the dry analytical element of Example 1 or Comparative Example 1. Respective analytical elements were incubated at 37° C. for 6 minutes, and their reflection optical densities (ODr) were measured at the wavelength of 600 nm from the support side.

The results are summarized in Table 5.

TABLE 5

| Creatinine Conc. (mg/dL) | ODr (Ex. 1) | ODr (C. Ex. 1) |
|---|---|---|
| 0 | 0.280 | 0.280 |
| 0.84 | 0.346 | 0.338 |
| 2.15 | 0.496 | 0.465 |
| 4.51 | 0.716 | 0.698 |
| 8.24 | 0.970 | 0.950 |
| 12.68 | 1.183 | 1.099 |

Figure 1:
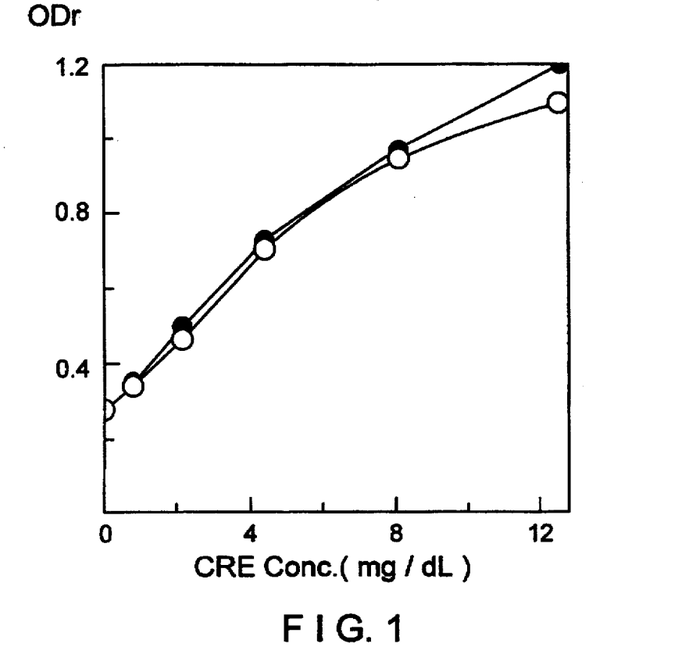
FIG. 1 is a graph indicating a relationship between creatinine concentration and reflection optical density measured by using an example of a dry analytical element of the invention (●) and a comparative dry analytical element (o).

The above results were made into a graph shown in FIG. 1 wherein ● indicates Example 1 and ○ indicates Comparative Example 1, respectively.

Subsequently, 10 μL of aqueous solution containing ammonia in a concentration shown in Table 6 was spotted, and measurement was conducted similarly. Using the curve shown in FIG. 1 as a calibration each measured reflection optical density was converted to apparent creatinine concentration. The results are summarized in Table 6.

TABLE 6

| Ammonia Conc. (mg/dL) | Example 1 (mg/dL) | Comparative Example 1 (mg/dL) |
|---|---|---|
| 0 | 0.10 | 0.10 |
| 100 | 0.12 | 0.25 |
| 300 | 0.13 | 0.38 |
| 500 | 0.17 | 0.52 |
| 1000 | 0.22 | 0.98 |

Figure 2:
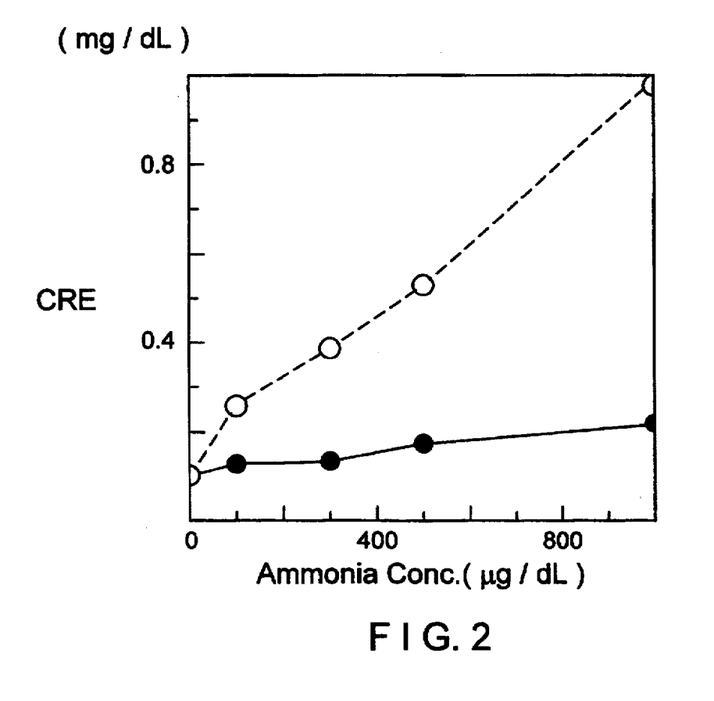
FIG. 2 is a graph indicating a relationship between ammonia concentration and reflection optical density measured by using an example of a dry analytical element of the invention (●) and a comparative dry analytical element (o) wherein the reflection optical density was converted to creatinine concentration using the graph of FIG. 1 as a standard curve (or a calibration curve).

The above results were made into a graph shown in FIG. 2 wherein ● indicates Example 1 and ○ indicates Comparative Example 1, respectively.

As can be seen Table 6 and FIG. 2, it is apparent that the analytical element of Example 1 is much resistant to positive error due to aqueous ammonia solution, i.e. has a high ability of removing ammonia, compared with the analytical element of Comparative Example 1.

Example 2

A dye-forming layer was provided on a colorless transparent smooth polyethylene terephthalate (PET) film (support) 180 μm in thickness provided with a gelatin undercoat layer by applying so as to become the coating amount shown in Table 7, followed by drying.

TABLE 7

| Dye-Forming Layer Composition | |
|---|---|
| Deionized gelatin | 12.0 g/m² |
| Horceradish peroxidase optimum pH: 6.5 | 9.1 KU/m² |
| 4-Aminoantipyrine | 0.59 g/m² |
| 1,7-Dihydroxynaphthalene | 0.21 g/m² |

(pH 6.5)

The dye-forming layer was damped by supplying 30 g/m² of water, and a tricot knitted fabric about 250 μm in thickness made by knitting pure polyethylene terephthalate spun yarn corresponding to 100s was laminated by lightly pressing almost uniformly to provide a spreading layer. On the spreading layer, the reagent composition shown in Table 8 was applied, and then dried to complete a dry analytical element for the determination of glucose.

TABLE 8

| Reagent Composition | |
|---|---|
| Polyvinyl pyrrolidone average molecular weight: 360,000 | 5.5 g/m² |
| Octylphenoxypolyethoxyethanol containing 9–10 hydroxyethylene unit on average | 0.5 g/m² |
| Ampholyte* | 1 g/m² |
| Glucose Oxidase optimum pH: 5.0 | 3 KU/m² |

(pH 5.0)

$$*R-NH+CH_2CH_2N)_5H$$
$$\qquad\qquad\qquad\quad R$$
R: $-CH_2CH_2COOH$
$-COOH$ : $-NH-$ = 6:6

Comparative Example 2

An analytical element for the determination of glucose was prepared similar to Example 2 except that the following reagent composition was used instead of the reagent composition of Table 8.

TABLE 9

| Reagent Composition | |
|---|---|
| Polyvinyl pyrrolidone average molecular weight: 360,000 | 5.5 g/m² |
| Octylphenoxypolyethoxyethanol containing 9–10 hydroxyethylene unit on average | 0.5 g/m² |
| MES | 1 g/m² |
| Glucose Oxidase optimum pH: 5.0 | 3 KU/m² |

Measurement 2

In order to examine quantitative determination ability of the dry analytical element of Example 2 and Comparative Example 2, the following test was conducted.

10 μL of each aqueous glucose solution containing glucose in a concentration shown in Table 10 was spotted onto the dry analytical element of Example 2 or Comparative Example 2. Respective analytical elements were incubated at 37° C. for 4 minutes, and their reflection optical density (ODr) was measured at the wavelength of 505 nm from the support side. The results are summarized in Table 10, and shown in FIG. 3 wherein ● indicates Example 2 and ○ indicates Comparative Example 2, respectively.

TABLE 10

| Glucose Conc. (mg/dL) | ODr (Ex. 2) | ODr (C. Ex. 2) |
|---|---|---|
| 0 | 0.10 | 0.10 |
| 100 | 0.32 | 0.28 |
| 230 | 0.59 | 0.46 |
| 480 | 0.87 | 0.65 |
| 620 | 1.00 | 0.70 |

Figure 3:
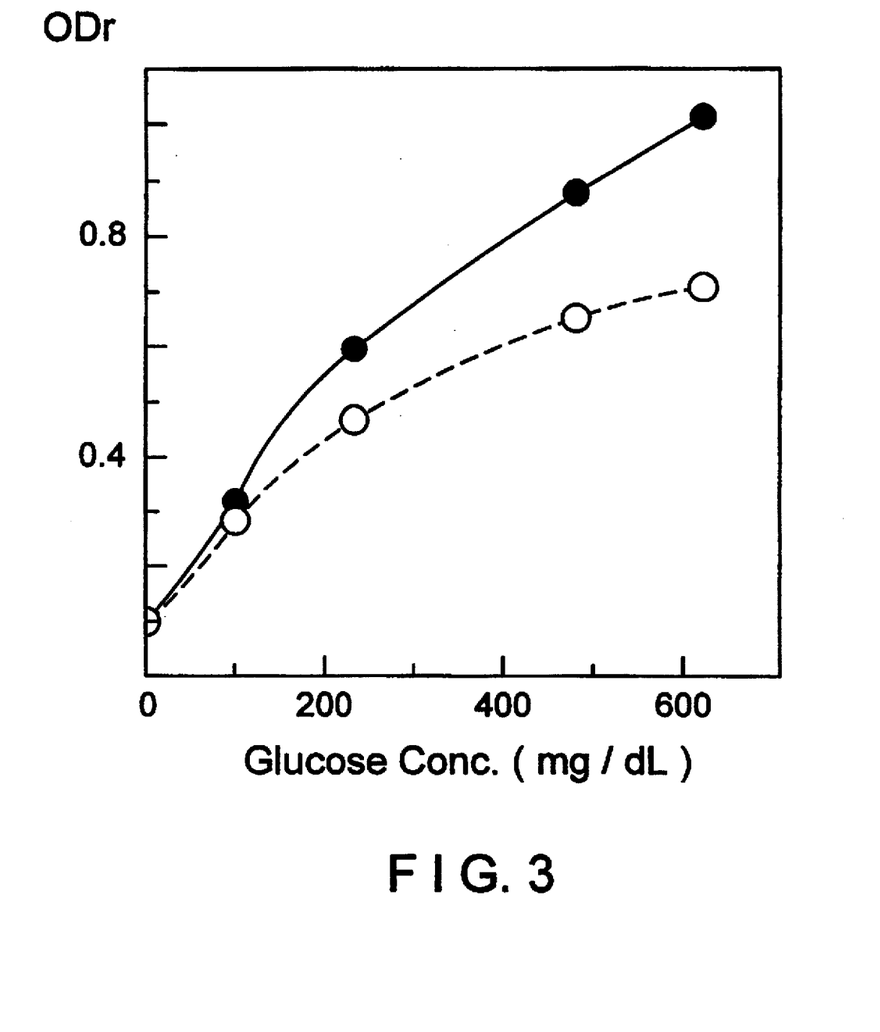
FIG. 3 is a graph indicating a relationshiop between glucose concentration and reflection optical density measured by using an example of a dry analytical element of the invention (●) and a comparative dry analytical element (o).

As can be seen from Table 10 and FIG. 3, it is apparent that the dry analytical element of Example 2 is superior in quantitative determination ability to Comparative Example 2.

Example 3

An indicator layer was provided by applying the following composition using ethanol as the solvent onto a colorless transparent smooth polyethylene terephthalate film (support) 180 μm in thickness so as to become the coating amount described in Table 11, followed by drying.

TABLE 11

| Indicator Layer Composition | |
|---|---|
| Polyvinyl methyl ether weight average molecular weight: about 40,000 | 2.2 g/m² |
| Bromophenol Blue | 0.14 g/m² |
| Sodium hydroxide | 8.4 g/m² |

A liquid barrier layer was provided thereon by pressing uniformly a membrane filter made of polyethylene having an average pore size of 0.2 min, a void content of 75% and a thickness of 100 μm.

An ammonia-producing reagent layer was provided further thereon by applying the following composition using water as the solvent so as to become the coating amount described in Table 12, followed by drying.

TABLE 12

| Ammonia-Producing Reagent Layer Composition | |
|---|---|
| Hydroxyethyl cellulose average molecular weight; about 40,000 average substitution degree; 1.0~1.3 | 5 g/m² |
| Sodium tetraborate | 1 g/m² |
| Creatinine iminohyrolase (E.C. 3,5,4,21) Optimum pH: 9.0 | 1,800 U/m² |

(pH 9.0)

An ammonia diffusion-preventing layer was provided by applying the following composition using water as the solvent so as to become the following coating amount, followed by drying.

| | |
|---|---|
| Hydroxypropyl cellulose methoxyl group: 28~30% hydroxypropoxyl groupo: 7~12% viscosity of 2% aqueous solution: 50 cps at 20° C. | 20 g/m² |

An endogeneous ammonia-trapping layer was provided thereon by applying the following composition using water as the solvent so as to become the coating amount described in Table 13, followed by drying.

TABLE 13

| Endogeneous Ammonia - Trapping Layer Composition | |
|---|---|
| Hydroxyethyl cellulose | 4 g/m² |
| Ampholyte* | 1 g/m² |
| α-Ketoglutaric acid.2Na salt | 1 g/m² |
| NADPH | 0.6 g/m² |
| glutamate dehydrogenase (E.C. 1,4,1,4) optimum pH: 8.0 | 10,000 U/m² |

(pH 8.2)

R:H or $-CH_2CH_2COOH$
$-COOH$: $-NH-$ and $-NH_2 = 2:6$

Subsequently, the endogeneous ammonia-trapping layer was damped by supplying 30 g/m² water, and a tricot knitted fabric made of pure polyethylene terephthalate (knitted by spun yarn corresponding to 100 S) about 250 μm in thickness was laminated thereon by pressing lightly and almost uniformly. The following composition was impregrated into the knitted fabric by applying as an ethanol solution and then dried to provide a spreading layer.

TABLE 14

| Hemalytic Reagent-Spreading Controller Composition | |
|---|---|
| Polyvinylpyrrolidone (average molecular weight; 360,000) | 7.8 g/m² |
| Triton X-100 | 8 g/m² |

Thus, a dry analytical element for the determination of creatinine was completed.

Comparative Example 3

A dry analytical element for the determination of creatinine was prepared similar to Example 3, except that Triton X-100 was omitted from the composition of Table 14.

Measurement 3

In order to examine hematocrit dependency of the dry analytical element of Example 3 and Comparative Example 3, the following test was conducted.

Figure 4:
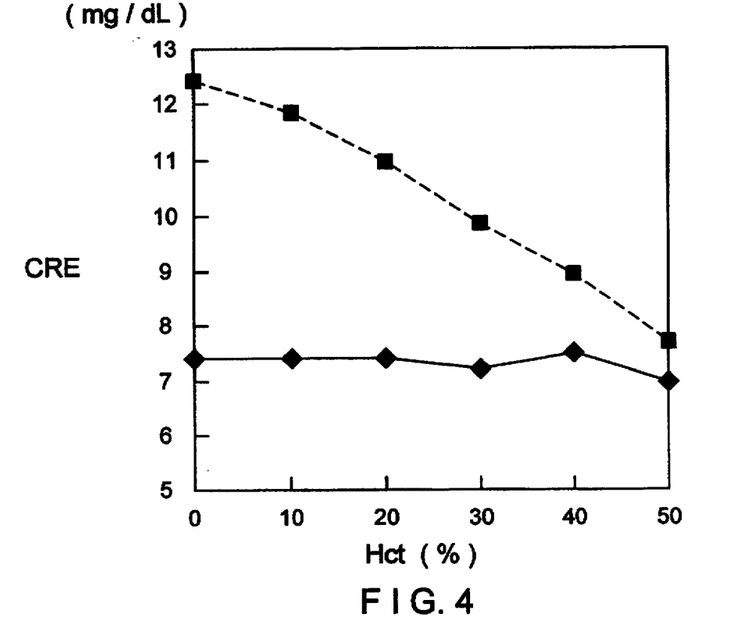
FIG. 4 is a graph indicating a relationship between apparent creatinine concentration converted from reflection optical density measured by using an example of a dry analytical element of the invention (full line) and a comparative dry analytical element (broken line).

A plasma sample (hematocrit value: 0%) and whole blood samples having a hematocrit value of 10%, 20%, 30%, 40% or 50% were prepared from a human whole blood sample containing 7.5 mg/dL creatinine. 10 μL of each sample 5 was spotted onto the dry analytical element of Example 3 or Comparative Example 3. Respective analytical elements were incubated at 37° C. for 6 minutes, and their reflection optical densities (ODr) were measured at the wavelength of 600 nm from the support side. The reflectionoptical densities were converted to creatinine concentration and shown in Table 15 and FIG. 4 wherein ● indicates Example 1 and o indicates Comparative Example 1, respectively.

TABLE 15

| Hematocrit (%) | Creatinine Conc. | |
|---|---|---|
| | Example 3 | Comparative 3 |
| 0 | 7.4 | 12.7 |
| 10 | 7.4 | 11.8 |
| 20 | 7.4 | 11.9 |
| 30 | 7.2 | 9.8 |
| 40 | 7.5 | 8.9 |
| 50 | 7.0 | 7.7 |

As can be seen from the above results, by using the analytical element of the invention, creatinine concentration can be determined accurately irrespective of hematocrit values at least in the range from 0% to 50%. On the other hand, in the ease of the comparative analytical element, creatinine concentration values were very inaccurate, and different from the true concentration of 7.5 mg/dL by about 20% to 70% with decreasing the hematocrit value from 40% to 0%.

Example 4

A reagent layer for the determination of glucose was provided on a colorless transparent smooth polyethylene terephthalate (PET) film (support) 180 μm in thickness by applying an aqueous solution of the following reagent composition for the determination of glucose so as to become the coating amount shown in Table 16, followed by drying.

TABLE 16

| Reagent Layer Composition | |
|---|---|
| Deionized gelatin | 19 g/m² |
| 1,7-Dihydroxynaphthalene | 180 g/m² |
| 4-Aminoantipyrine derivative* | 950 g/m² |
| glucose oxidase | 6,600 U/m² |
| Peroxidase | 20,000 U/m² |

*4-amino-2,3-dimethyl-1-(2,4,6-trichlorophenyl)-3-pyrazoline-5-one (Japanese Patent KOKAI 59-54962)

The reagent layer was damped by supplying 30 g/m² of water, and a tricot knitted fabric about 250 μm in thickness made by knitting pure polyethylene terephthalate spun yarn corresponding to 100s was laminated by lightly pressing almost uniformly to provide a spreading layer. On the spreading layer, an ethanol solution of the composition shown in Table 17 was applied, and then dried to complete a dry analytical element for the determination of glucose.

TABLE 17

| Hemolytic Reagent-Sptreading Controller Composition | |
|---|---|
| Triton X-100 | 8.0 g/m² |
| Polyvinyl pyrrolidone average molecular weight: 360,000 | 7.8 g/m² |

Comparative Example 4

An analytical element for the determination of glucose was prepared similar to Example 4 except that the hemolytic reagent component was omitted from the composition of Table 17.

Measurement 4

In order to examine hematocrit dependency of the dry analytical element of Example 4 and Comparative Example 4, the following test was conducted.

Figure 5:
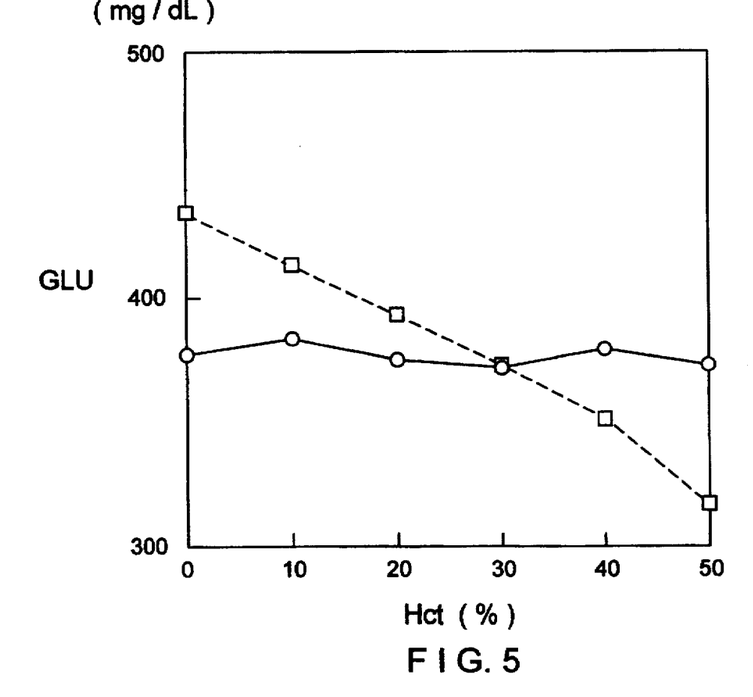
FIG. 5 is a graph indicating a relationship between apparent glucose concentration converted from reflection optical density measured by using an example of a dry analytical element of the invention (full line) and a comparative dry analytical element (broken line).

A plasma sample (hematocrit value: 0%) and whole blood samples having a hematocrit value of 10%, 20%, 30%, 40% or 50% were prepared from a human whole blood sample containng 380 mg/dL glucose. 10 μL of each sample was spotted onto the dry analytical element of Example 4 or Comparative Example 4. Respective analytical elements were incubated at 37° C. for 6 minutes, and their reflection optical density (ODr) was measured at the wavelength of 550 nm from the support side. The reflection optical densities were converted to glucose concentration and shown in Table 18, and shown in FIG. 5 wherein ● indicates Example 4 and ○ indicates Comparative Example 4, respectively.

TABLE 18

| Hematocrit | Glucose Conc. | |
|---|---|---|
| (%) | Example 4 | Comparative 4 |
| 0 | 378 | 436 |
| 10 | 385 | 415 |
| 20 | 376 | 394 |
| 30 | 372 | 373 |
| 40 | 381 | 351 |
| 50 | 374 | 317 |

As can be seen from the above results, by using the analytical element of the invention, glucose concentration can be determined accurately irrespective of hematocrit values at least in the range from 0% to 50%. On the other hand, in the case of the comparative analytical element, although accurate values within a difference of about 3.7% or less from the true concentration of 380 mg/dL in the range of the hematocrit value of 20 to 30%, in the other range, the measured values were very inaccurate, and different from the true value by about 9 to 15% in the range from the plasma to hematocrit value of 10%, and by about 8 to 17% in the range from 40 to 50% of hematocrit values.

We claim:

1. A dry analytical element comprising, laminated in this order, a support, at least one water-permeable reagent layer and a porous spreading layer, wherein at least one layer contains a water-soluble polybasic amino carboxylic acid which is an ampholyte having the formula R—NH—($CH_2CH_2$—N)—$_n$H, wherein R is H or —($CH_2$—)$_m$COOH, provided that m is 1 or 2, and n is 3, 4 or 5.

2. The dry analytical element of claim 1, wherein said n is 5, R is H or —$CH_2CH_2$COOH and the molar ratio of —COOH:—NH— and —$NH_2$ is 1:6 to 6:6.

3. The dry analytical element of claim 1, wherein the layer containing said ampholyte is adjusted so as to have a predetermined pH value in a range of pH 5.0 to 9.5 upon spotting a liquid sample.

4. The dry analytical element of claim 1, wherein said support is a water-impermeable transparent support.

5. The dry analytical element of claim 1 which further comprises an additional water-permeable layer, which layer contains the ampholyte.

6. The dry analytical element of claim 1, wherein said ampholyte is a water-soluble polybasic amino carboxylic acid synthesised by reacting an organic compound having at least two amino or imino groups reacting with a carboxylic acid ester having a carbon-carbon double bond in a non-aqueous solvent, and then hydrolyzing the ester portion.

7. The dry analytical element of claim 6, wherein the layer containing said ampholyte is adjusted so as to have a predetermined pH value in a range of pH 5.0 to 9.5 upon spotting a liquid sample.

8. The dry analytical element of claim 6, wherein said support is a water-impermeable transparent support.

9. The dry analytical element of claim 6, which consists essentially of a water-impermeable transparent support, an indicator layer, a porous liquid barrier layer, an ammonia-producing reagent layer, an ammonia diffusion-preventing layer, an endogeneous ammonia-trapping layer, and the spreading layer integrally laminated in this order, wherein said ampholyte is incorporated into the endogeneous ammonia-trapping layer.

10. The dry analytical element of claim 8, wherein a reagent composition for the detection of creatinine is incorporated into the ammonia-producing reagent layer.

11. The dry analytical element of claim 1 comprising at least one water-permeable reagent layer and a porous spreading layer for spreading whole blood wherein the spreading layer contains a hemolytic reagent.

12. The dry analytical element of claim 11 which contains a reagent composition for determination of a member selected from the group consisting of creatinine, urea nitrogen, inorganic phosphorus and bicarbonate salts.

13. The dry analytical element of claim 11 which contains a reagent composition for the determination of creatinine or urea nitrogen.

14. The dry analytical element of claim 11, wherein said hemolytic reagent is a surfactant.

15. The dry analytical element of claim 14, wherein the content of said surfactant is 1 to 50 $g/m^2$.

16. The dry analytical element of claim 14, wherein the content of said surfactant is 1 to 50 $g/m^2$.

17. The dry analytical element of claim 14, wherein said surfactant is a nonionic surfactant.

18. The dry analytical element of claim 17, wherein said nonionic surfactant is alkylphenoxypolyethoxyethanol.

19. A dry analytical element which consists essentially of a water-impermeable transparent support, an indicator layer, a porous liquid barrier layer, an ammonia-producing reagent layer, an ammonia diffusion-preventing layer, an endogenous ammonia-trapping layer, and a spreading layer, integrally laminated in this order, and having an ampholyte having the formula R—NH—$(CH_2CH_2$—N$)_n$H, wherein R is H or —$(CH_2)_m$COOH, provided that m is 1 or 2, and n is 3, 4 or 5 incorporated into the endogenous ammonia-trapping layer.

20. The dry analytical element of claim 19, wherein a reagent composition for the detection of creatinine is incorporated into the ammonia-producing reagent layer.

* * * * *